(12) United States Patent
Popescu et al.

(10) Patent No.: US 7,634,047 B2
(45) Date of Patent: Dec. 15, 2009

(54) COMPUTED TOMOGRAPHY SYSTEM WITH STATIONARY ANODE RING

(75) Inventors: Stefan Popescu, Erlangen (DE); Georg Wittmann, Herzogenaurach (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 12/179,702

(22) Filed: Jul. 25, 2008

(65) Prior Publication Data

US 2009/0028292 A1    Jan. 29, 2009

(30) Foreign Application Priority Data

Jul. 27, 2007    (DE)    ........................ 10 2007 035 177

(51) Int. Cl.
*A61B 6/00*    (2006.01)

(52) U.S. Cl. ............................................. 378/19; 378/4

(58) Field of Classification Search ........................ 378/4, 378/9, 19, 15, 20, 62, 64, 68, 119, 123, 134–138
See application file for complete search history.

(56) References Cited

U.S. PATENT DOCUMENTS

| | | | |
|---|---|---|---|
| 4,158,142 A | 6/1979 | Haimson | |
| 4,346,330 A | 8/1982 | Lee et al. | |
| 4,352,021 A | 9/1982 | Boyd et al. | |
| 4,521,900 A | 6/1985 | Rand | |
| 4,521,901 A | 6/1985 | Rand | |
| 4,606,061 A | 8/1986 | Ramamurti | |
| 4,821,305 A | 4/1989 | Anderson | |
| 5,125,012 A | 6/1992 | Schittenhelm | |
| 5,191,600 A | 3/1993 | Vincent et al. | |
| 5,195,112 A | 3/1993 | Vincent et al. | |
| 5,305,363 A * | 4/1994 | Burke et al. | 378/4 |
| 5,493,599 A * | 2/1996 | Mattson | 378/147 |
| 5,966,422 A | 10/1999 | Dafni et al. | |
| 7,016,455 B2 | 3/2006 | Bruder et al. | |
| 7,123,689 B1 | 10/2006 | Wilson | |
| 7,340,029 B2 | 3/2008 | Popescu | |
| 2006/0002514 A1 | 1/2006 | Dunham | |
| 2006/0159221 A1 | 7/2006 | Popescu | |
| 2007/0086571 A1 | 4/2007 | Hempel et al. | |

FOREIGN PATENT DOCUMENTS

EP    0 377 070    7/1990

* cited by examiner

*Primary Examiner*—Irakli Kiknadze
(74) *Attorney, Agent, or Firm*—Schiff Hardin LLP

(57) ABSTRACT

A computer tomography system has a stationary x-ray tube, that has an anode ring and at least one cathode ring, that extends through 360° in a system plane perpendicular to a system axis, and a vacuum region that is at least partially delimited by a light-permeable and/or infrared-permeable vacuum window is provided between the anode ring and the at least one cathode ring. A support frame is rotatable around the system axis parallel to the system plane, on which are arranged, in at least one angle position, a system with at least one laser for local activation of electron emission at the at least one cathode ring, and a filter and/or collimator set, and a radiation detector opposite the filter and collimator set.

23 Claims, 4 Drawing Sheets

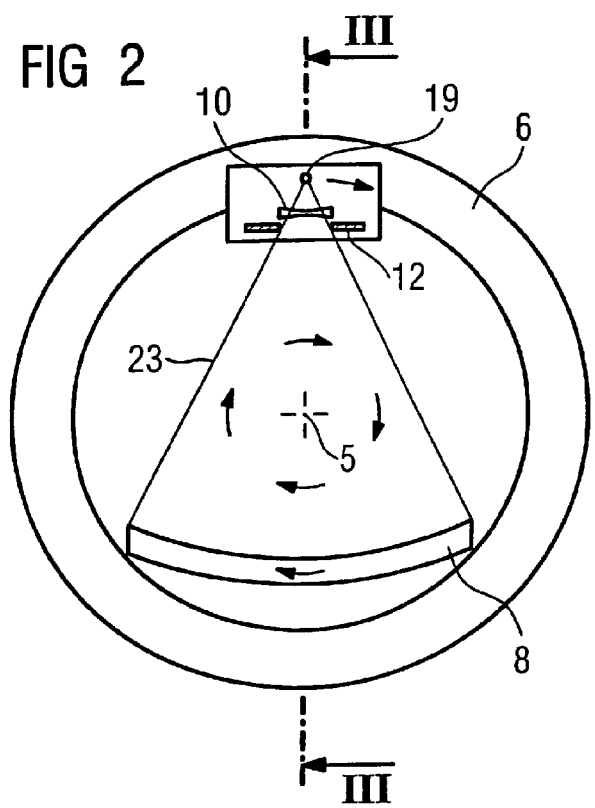
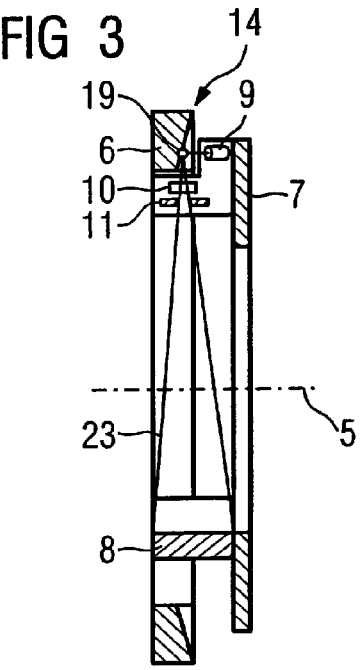
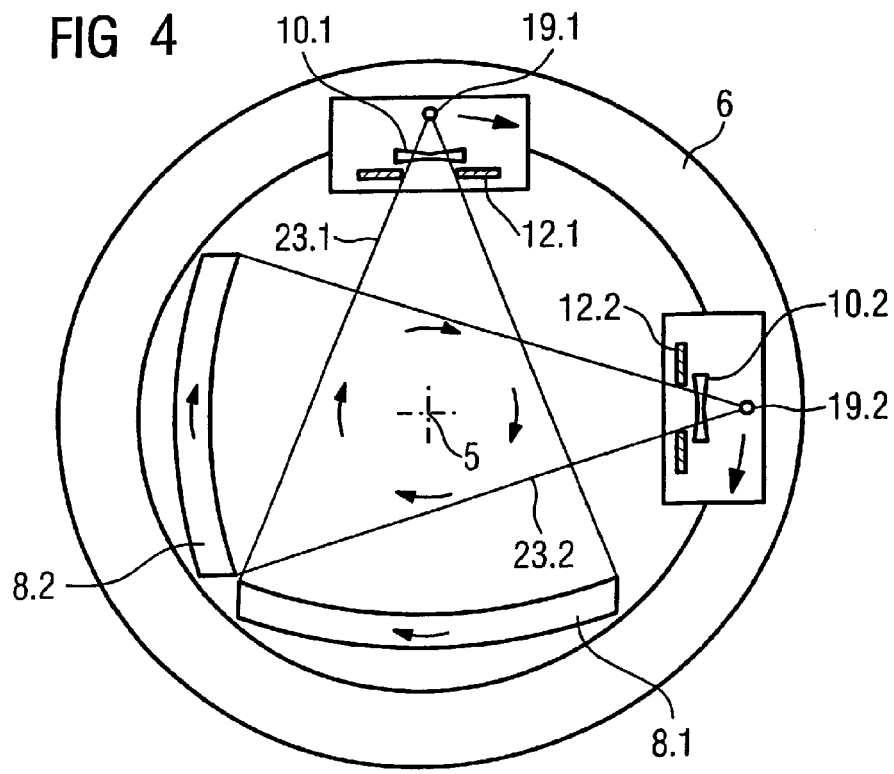

COMPUTED TOMOGRAPHY SYSTEM WITH STATIONARY ANODE RING

BACKGROUND OF THE INVENTION

1. Field of the Invention

The present invention concerns a computed tomography (CT) system with a stationary anode ring, of the type known as fifth-generation computed tomography systems.

2. Description of the Prior Art

DE 10 2004 061 347 B3 discloses an example of a CT system of this type. This patent document describes a CT system of the fifth generation in which x-ray radiation is generated at a stationary anode ring with the use of a directed electron beam, which x-ray radiation is pre-filtered with the aid of a bowtie filter and collimators and strikes an oppositely situated detector, likewise mounted on a support frame. The support frame is continuously aligned with the rotating x-ray focus that is generated by the electron beam, so that the x-ray fan that is emitted always passes in the same way through the filter mounted on the support frame and strikes the detector.

Such a CT system is very complicated in design since the electron beam that is generated requires a complex deflection device in order to align it appropriately on the anode ring. Furthermore, spatial problems occur in such a CT system since the electron beam emitter must be arranged in the region of the system axis. The free displacement capability of a patient bed or subject table is severely hindered by this arrangement. An even higher cost expenditure is required if the electron source is placed elsewhere, in order to concentrate the electron beam over a significantly longer distance and direct it to the anode. The use of a stationary detector covering 270° to 360°, as is typical in fifth-generation CT systems, is also very complicated.

Third generation CT systems also are known wherein an x-ray tube is mounted on a rotating gantry or support frame. This requires a support frame with very complicated bearing in order to handle the centrifugal forces that arise due to the rotation of x-ray tube. Furthermore, in such an embodiment of a CT system it is necessary to supply high voltage to the x-ray tube via costly slip rings.

United States Patent Application Publication No. 2006/0002514 A1 and EP 0 377 070 A1 describe further examples of such known CT systems.

SUMMARY OF THE INVENTION

An object of the present invention is to simplify a system in which the x-ray tube need not be mounted on a support frame, and wherein no spatial limitations exist as is the case given use of electron beam emitters with corresponding devices for redirection and concentration of the electron beam.

The above object is achieved in accordance with the invention by a computed tomography system that has a stationary anode ring but does not use a thermionic electron beam emitter (gun). The stationary anode ring is mounted opposite a cathode ring that is selectively excited with the use of a laser for electron emission. An electrical field is generated between the anode ring and the cathode ring, so that x-rays are emitted from successive foci on the anode ring. The excitation of the electron emission is generated by a laser that is very light in relation to the x-ray tube. This laser can be mounted on the support frame that carries a filter with a collimator and an oppositely situated detector. In order to be able to implement the electron emission excitation with the use of a laser, it is necessary to equip the vacuum region in which the anode ring and cathode ring are mounted with a light-permeable window so that the laser light can strike the cathode ring. There are different possibilities with regard to the geometric arrangement of the anode ring and the cathode ring. One possibility is to irradiate the cathode ring on its back side so that the electrons are emitted from the front side thereof in the direction of the anode. It is also possible, with an appropriate geometric arrangement of the laser and the cathode ring and the anode ring, to excite the cathode ring from the emission side (thus from the front side) with the laser beam, allowing a higher electron yield to be achieved.

In accordance with the invention, a computed tomography system has a stationary x-ray tube having an anode ring and at least one cathode ring, the x-ray tube extending through 360° in a system plane perpendicular to a system axis. A vacuum region that is at least partially delimited by a light-permeable and/or infrared-permeable vacuum window is provided between the anode ring and the at least one cathode ring. Furthermore, this computed tomography system according to the invention has a support frame that is rotatable around the system axis parallel to the system plane, on this support frame, in at least one angle position, a system with a laser is attached (mounted) for local activation of electron emission at the cathode ring, as well as a filter and/or collimator set. A radiation detector is arranged opposite the filter and collimator set on the support frame.

In this embodiment of a computed tomography system according to the invention, electron emission spots that "rotate" along the cathode ring are generated with the use of a laser system mounted on the rotatable support frame, the "rotation" of the electron emission spots being synchronous to the rotation of the support frame. If a cathode of the type known as a multi-emitter cathode is used, the laser can also simply be used as a position sensor in connection with photoswitches on the side of the stationary cathode ring, or another position sensor (for example a Hall sensor) can be used, in order to release an electron emission on the periphery at the desired position.

A "rotating" focus arises on the anode ring corresponding to the position of the activated electron emission, from which focus x-ray radiation is emitted that is limited (with regard to the beam fan) by the collimator set likewise attached on the support frame, and with the use of a bowtie filter. The x-ray radiation beam thus can be optimally adapted to the requirements of the employed detector. Such a system including laser and a filter and/or a collimator set is significantly lighter than an x-ray tube as is conventionally used on the gantry of third generation CT systems. A simpler and lighter design of the support frame thus is possible. By contrast, if the conventional "heavy duty" support frame is a retained, the support frame can rotate significantly faster given the inventive light weight design of the x-ray source, so higher scan speeds are possible, which is particularly advantageous in the field of cardio-CT.

According to the invention, the light-permeable and/or infrared-permeable vacuum window can be fashioned as a quartz window.

In a first embodiment of the computed tomography system according to the invention wherein the excitation of the electron emission occurs from the back side of the cathode ring, it is proposed that the cathode ring extends on the inside of the light-permeable and/or infrared-permeable vacuum window, and the light beam emitted by the laser strikes the cathode ring on the side facing the vacuum window while the electrons are emitted on the side facing the anode ring.

Such an embodiment has the advantage that the cathode ring can be optimally positioned relative to the anode ring, but the disadvantage is that a somewhat reduced electron yield occurs relative to laser exposure of the front side of the cathode ring.

Therefore, in a second embodiment of the computed tomography system according to the invention in which the front side of the cathode ring is irradiated by the laser. In this embodiment the cathode ring is arranged opposite the light-permeable and/or infrared-permeable vacuum window, and the laser is aligned such that a laser beam strikes the surface of the cathode ring that faces the anode and on which the electron emission occurs.

Depending on the positioning of the laser, for example, it can also be advantageous to arrange at least one mirror surface between the laser and the cathode ring, the mirror surface deflecting the laser beam toward the cathode surface. This at least one mirror surface can be arranged within the vacuum region of the x-ray tube. It is advantageous for this at least one mirror surface to be fashioned also as a ring.

If this mirror surface is located within the vacuum region, it is advantageous to connect this mirror surface to a negative potential so that electrons or particles that are emitted from the cathode do not strike the mirror surface and contaminate this surface.

Alternatively, at least one mirror surface can be arranged outside of the vacuum region, for example to enable a simpler positioning of the laser system on the support frame, or possibly to be able to execute a variable deflection of the laser beam. For example, different emission spots can be illuminated on the cathode ring in order to be able to achieve an effect similar to the flying focal spots in conventional CT systems.

Although the CT system described in the preceding corresponds in terms of basic function to a computed tomography system of the third generation with a focus-detector system, it departs therefrom by having an additional system composed of a laser for activation of electron emission at the cathode ring, an additional filter and/or collimator set, and an additional detector opposite the filter and collimator set can also be attached at at least one further angle position at the computed tomography system according to the invention. It is thus possible to increase the scan rate of the CT system. The multiple focus-detector systems can either exhibit identical fan angles or may be operated with different fan angles.

According to another embodiment of the computed tomography system according to the invention, at least one further cathode ring is provided that can be operated simultaneously with a different voltage from the first cathode ring. In this way it is possible to operate the CT system according to the invention as a multiple energy scanner. For example, a first system composed of a laser, filter and opposite detector, can be is operated in connection with a first cathode ring at a first voltage, while a second system composed of another laser, filter and detector is operated with a second cathode ring that is at a second voltage. The at least one additional laser/filter/detector system has the features described above for the first laser/filter/detector system.

Furthermore, it is advantageous for the computed tomography system to have a detector or detectors that is/are fashioned as multi-line detectors.

It is also advantageous to provide the stationary anode ring with at least one cooling channel in order to ensure a sufficient cooling even at higher load.

In another embodiment of the computed tomography system according to the invention, that the at least one cathode ring is formed by at least two segments that can be individu-ally charged with different voltages. This design also enables scanning with different x-ray energies to be implemented in a simple manner.

The above object also is achieved in accordance with the invention by the computed tomography system having a stationary x-ray tube having an anode ring and at least one cathode ring that is fashioned as a multi-emitter cathode, the x-ray tube extending through 360° in a system plane perpendicular to a system axis, with a vacuum region that is partially limited by at least one light-permeable and/or infrared-permeable vacuum window provided between the anode ring and the at least one cathode ring, a support frame that is rotatable around the system axis parallel to the system plane, on which are attached, in at least one angle position, a system with at least one position transmitter for local activation of electron emission at the at least one cathode ring forming a multi-emitter cathode, and a filter and/or collimator set, and a radiation detector opposite the filter and collimator set.

For example, a laser can be used as the position transmitter in connection with a number of photo-switches or Hall sensors, so the respective segments of the multi-emitter cathode are activated corresponding to the positioning of the position transmitter.

BRIEF DESCRIPTION OF THE DRAWINGS

FIG. 2 schematically shows a cross-section of the computed tomography system of FIG. 1 in the gantry region, with a laser/filter/detector system.

FIG. 3 is section A-A from FIG. 2.

FIG. 4 is a cross-section in the gantry region through a CT system according to the invention, with two laser/filter/detector systems.

DESCRIPTION OF THE PREFERRED EMBODIMENTS

Figure 1:
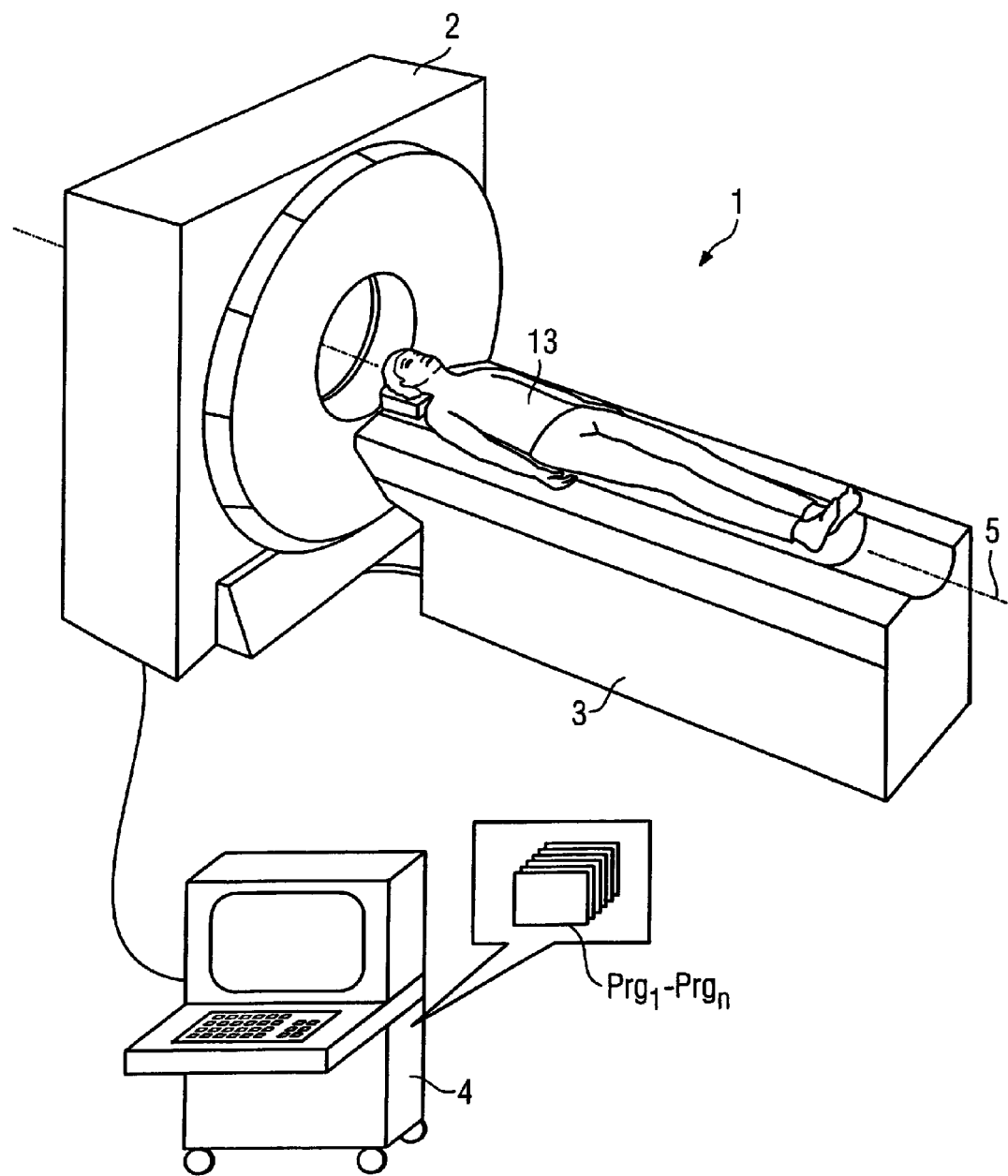
FIG. 1 schematically illustrates the basic components of a computed tomography system according to the invention.

In the following the invention is described in detail using preferred exemplary embodiments with the aid of the figures, wherein only the features necessary for understanding of the invention are presented. The following reference characters are used: 1: computer tomography system; 2: gantry housing; 3: patient bed; 4: control and computation unit; 5: system axis; 6: stationary anode ring; 7: rotatable support frame; 8: detector; 8.1: first detector; 8.2: second detector; 9: laser; 9.1: first laser; 9.2: second laser; 10: bowtie filter; 10.1: first bowtie filter; 10.2: second bowtie filter; 11: z-collimators; 11.1: first z-collimators; 11.2: second z-collimators; 12: (φ-collimators; 13: patient; 14: x-ray tube; 15: monitoring unit; 16.1: cooling channel; 16.2: cooling channel; 17: vacuum region; 18: quartz window; 18.1: first quartz window; 18.2: second quartz window; 19: focus; 19.1: first focus; 19.2: second focus; 20: laser beam; 20.1: first laser beam; 20.2: second laser beam; 21: cathode ring; 21.1: first cathode ring; 21.2: second cathode ring; 22: electron beam; 22.1: first electron beam; 22.2: second electron beam; 23: x-ray fan; 23.1: first x-ray fan; 23.2: second x-ray fan; 24: mirror; 24.1: first mirror; 24.2: second mirror; $Prg_1$-$Prg_n$: computer programs; ($\phi_1$, $\phi_2$): fan angles.

FIG. 1 shows an overview representation of a computed tomography (CT) system 1 according to the invention, with a gantry 2 that has a central measurement opening through which a patient 13 can be displaced with the use of a patient table 3 that is longitudinally displaceable in the direction of the system axis 5. The inventive embodiment of the x-ray tube and laser/filter/detector system on the gantry is located within the gantry housing 2 and is not visible here. The CT system 1 is operated by a control and computation unit 4, wherein operating programs $Prg_1$ through $Prg_n$ are stored in a memory. An evaluation of acquired detector data can also occur with the use of these operating programs. All methods used in the prior art for evaluation of the detector data for spiral scanning or sequential scanning can be employed here with single-line or multi-line detectors.

An exemplary first embodiment of an inventive design of an x-ray tube and of a laser/filter/detector system on a support frame is presented in FIGS. 2 and 3.

FIG. 2 shows a cross-section perpendicular to the system axis while FIG. 3 shows a longitudinal section parallel to the system axis. Shown therein is an x-ray tube having an anode ring 6 extending through 360°, which anode ring 6 has a focus 19 that travels 360° along the anode ring 6 with the rotation of the support frame 7. This focus 19 is generated by a laser 9 generating a hotspot on a cathode ring (not shown here) through a vacuum window (likewise not shown here) set in the x-ray tube, via which hot spot the cathode ring is excited to electron emission at points. Due to the applied potential difference between anode ring 6 and cathode ring, an electron beam is emitted that generates a focus on the anode side. X-ray radiation is generated that is directed as a radiation fan 23 emanating from the focus 19 toward an opposite detector 8. A filter and collimator set with a bowtie filter 10, which variably filters the radiation in the $\phi$-direction in order to obtain an improved dose utilization of the detector (as is known from x-ray tubes of third-generation CT systems) is located on the support frame 7 for filtering and delimitation of this radiation fan 23. Furthermore, a radiation delimitation of the fan beam 23 is produced with the use of ($\phi$-collimators 12 and z-collimators 11 that are likewise mounted on the rotating support frame 7, such that the beam fan covers the detector 8 in the desired manner. Due to the rotation of the support frame 7 which carries both the detector 8 and the laser 9 with the filter and collimator set 10, 11, 12, the excitation of the electron emission on the cathode (and therefore the focus) moves 360° around the system axis 5 on the anode ring, corresponding to the rotation of the support frame 7. (Although the focus 19 is shown within the box containing the filter and collimator set 10, 11, 12, the focus 19, as stated above, is on the anode ring 6 behind this box.) In this way it is possible to optimally filter the arising radiation as well as to execute the support frame significantly lighter due to the non-use of a heavy x-ray tube, is conventional as on the gantry in third-generation CT systems. It is also possible to significantly increase the rotation speed of the support frame due to the reduced g-forces in the region of the support frame 7.

The invention is not limited to a single laser/filter/detector system on the support frame 7; rather, multiple such systems in the sense of the invention can be arranged on the support frame 7, for example two systems offset by 90° or even three systems respectively offset by 120°. Only the size of the employed detectors is limiting, so it is advantageous (in particular with regard to the arising scatter radiation) to use two systems offset by 90°.

FIG. 4 shows such a computed tomography system according to the invention with two laser/filter/detector systems offset by 90° on a support frame in cross-section. Located on the support frame 7 (not visible here), with an offset of 90°, is a first filter/collimator set 10.1, 12.1 that filters a radiation fan 23.1 (emanating from a focus 19.1) and is directed toward an opposing detector 8.1. Arranged offset 90° to this is a second filter and collimator set 10.2, 12.2 that limits and filters a second radiation fan 23.2 emanating from a focus 19.2 to the opposing detector 8.2. The two radiation fans 23.1 and 23.2 exhibit different fan angles $\phi_1$ and $\phi_2$ in the example shown here. Embodiments with identically sized fan angles are also within the scope of the invention.

A detailed description of different embodiments of the stationary x-ray tube 14 extending through 360° and of the associated laser/filter system is presented in FIGS. 5 through 8.

Figure 5:
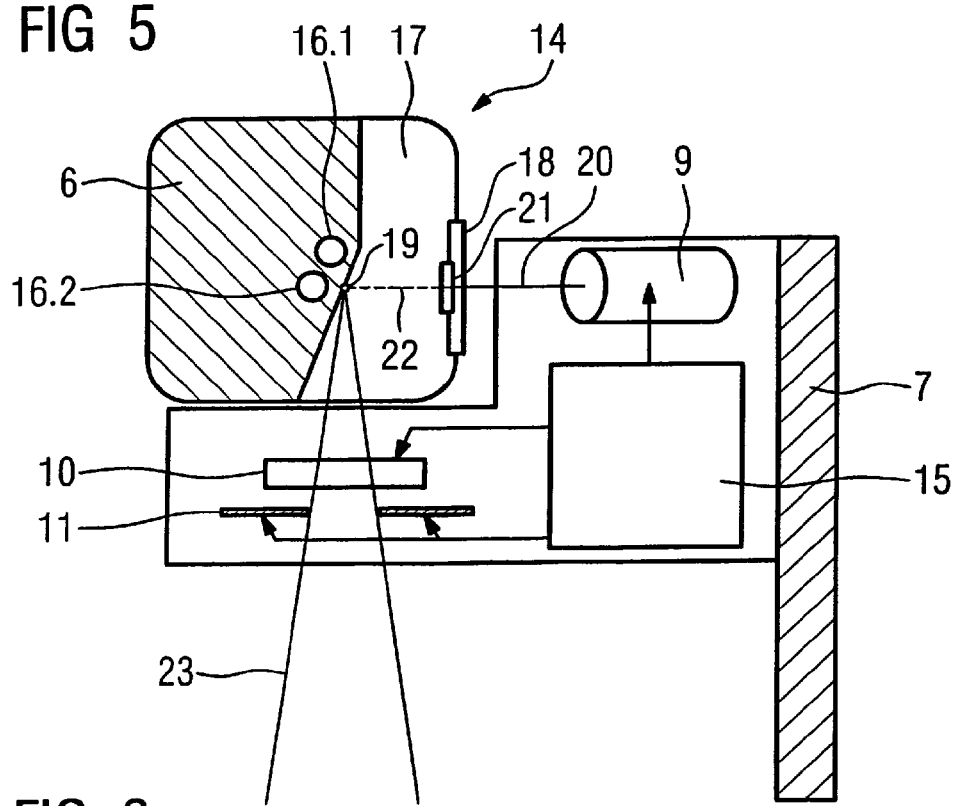
FIG. 5 is a longitudinal section through an x-ray tube and laser/filter region of a gantry, with excitation of the electron beam emission from the back side of the cathode ring, in accordance with the invention.

FIG. 5 shows a first simple variant. The x-ray tube 14 has an anode ring 6 in which two cooling channels 16.1 and 16.2 are arranged near the arising focus 19 for improved heat dissipation. The active anode surface with the focus 19 is located in a vacuum region 17 on whose opposite side is mounted a cathode ring 21 outwardly bounded by a vacuum window. Located on the support frame 7 is a laser 9 that emits a light beam 20 that passes through the vacuum window 18 and strikes the back side of the cathode ring 21. A hotspot arises due to the known embodiment of such a cathode ring (which are normally poorly heat-conductive materials), which leads to an electron emission on the front side of the cathode ring 21. Due to the applied potential difference between the cathode ring 21 and the anode ring 6, a strong electrical field arises which directs the emitted electrons as an electron beam 22 to an opposite focus 19. There the electrons are strongly braked and the x-ray radiation arises in a known manner. This is filtered and limited in the desired manner by the filter 10 and collimators 11 mounted on the anode ring 6, such that the desired radiation fan 23 arises. The control of the laser 9 and of the filter 10 and the collimator 11 is implemented via a monitoring unit 15 that here is likewise mounted on the support frame 7.

Figure 6:
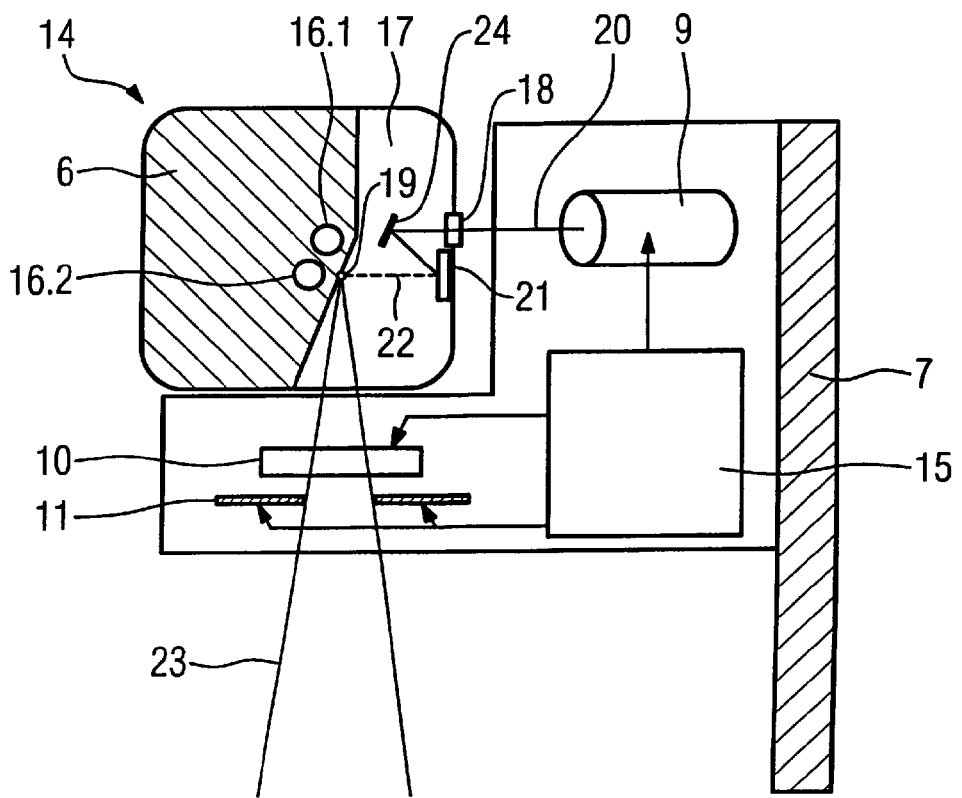
FIG. 6 is a longitudinal section through x-ray tube and laser/filter region of a gantry, with excitation of the electron beam emission from the front side of the cathode ring, in accordance with the invention.

An alternative embodiment of the x-ray tube according to the invention with a laser/filter system is shown in FIG. 6. This shows an embodiment similar to FIG. 5, but a mirror 24, which deflects the light beam 20 that emanates from the laser 9 and directs it to the front side of the cathode ring 21, is additionally located in the vacuum region 17. A hotspot therefore arises on the front side of the cathode ring 21, at which hot spot the electron emission is excited on the cathode ring 21 so that an x-ray fan 23 is generated as illustrated above.

In this context it is noted that the shown representations of the arrangement of the laser and of the cathode ring are only examples. Other positionings are also possible with different spatial relationships, and in particular with different radiation directions of the laser beam.

Figure 7:
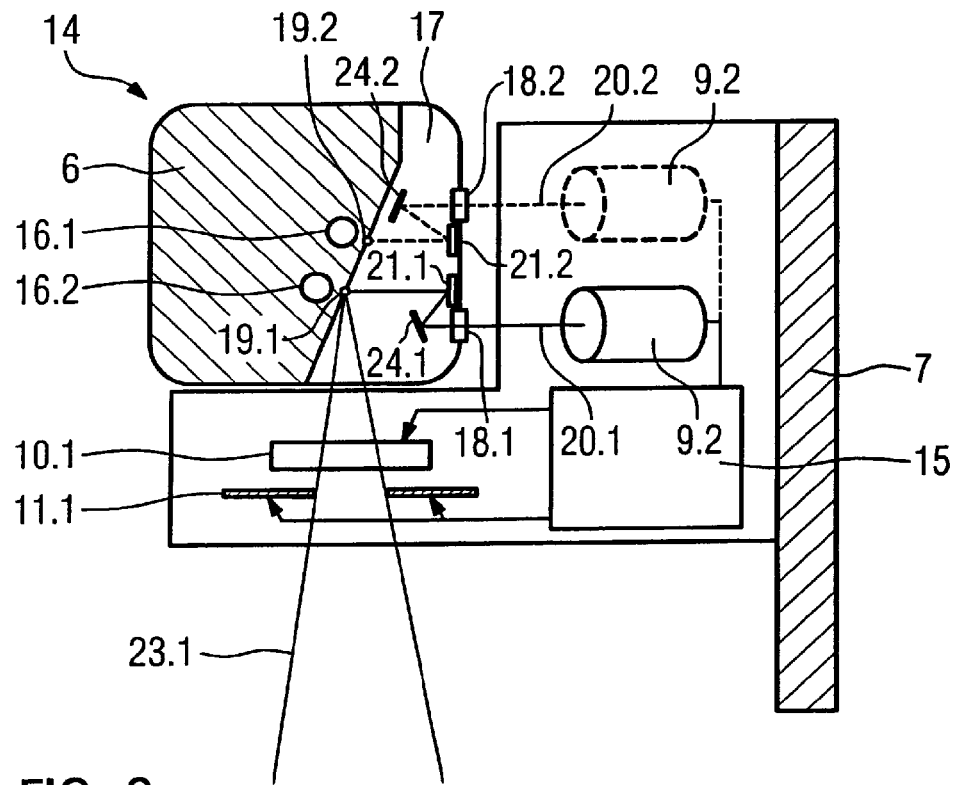
FIG. 7 is a longitudinal section through x-ray tube and laser/filter region of a gantry with two cathode rings, with excitation of the electron beam emission from the front side of the cathode rings, in accordance with the invention.
Figure 8:
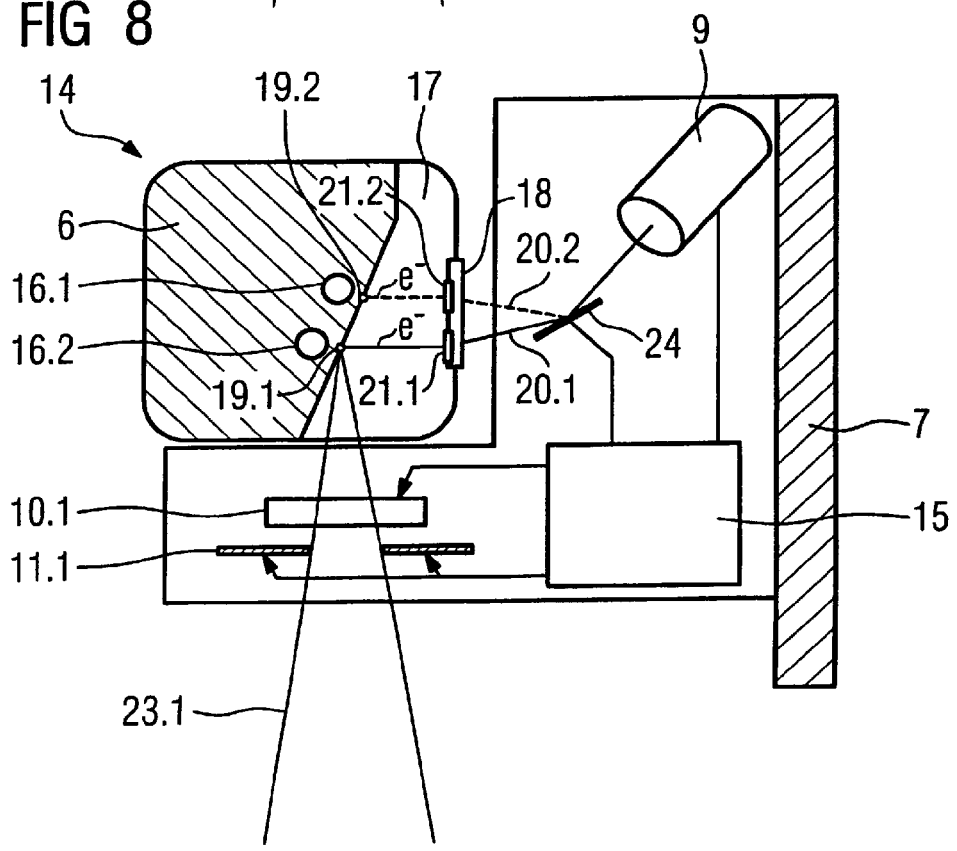
FIG. 8 is a longitudinal section through x-ray tube and laser/filter region of a gantry with two cathode rings, with excitation of the electron beam emission from the back side of the cathode rings in accordance with the invention.

While FIGS. 5 and 6 present embodiments of an x-ray tube with a single cathode ring, FIGS. 7 and 8 show variations with two cathode rings that can possibly be operated with different acceleration voltages.

FIG. 7 shows an embodiment variant of an x-ray tube with two cathode rings 21.1 and 21.2, wherein the light beams 20.1 and 20.2 of the laser can be deflected onto the front side of both cathode rings 21.1 and 21.2 with the use of two lasers 9.1 and 9.2 via to differently positioned windows 18.1 and 18.2, and with the use of two mirrors 24.1 and 24.2 positioned in the vacuum region 17, such that two foci 19.1 and 19.2 arise at different points of the anode ring 6. In the illustrates depiction, the second laser 9.2 (including the associated laser beam 20.2) and the arising electron beam are shown in dashed lines. This indicates that a specific angle position at which only one of the two laser systems is operated. The associated filters and collimators for the other system must naturally be adapted.

FIG. 8 shows a similar system, but wherein a single laser 9 emits a laser beam that can be deflected by an adjustable mirror 24 so that it excites either a first cathode ring 21.1 or a second cathode ring 21.2 (here from the back side) to electron emission, such that different x-ray energies also arise corresponding to different voltages respectively applied to the cathode rings. The collimators and filters 11.1 and 10.1 can also be positioned with the use of the monitoring device 15, corresponding to the actual cathode ring that is used and the different positions of the foci 19.1 and 19.2.

Overall, this embodiment according to the invention enables a combination of a stationary x-ray tube and a laser mounted on a support frame for spatially variable focus generation is computed tomography systems that can be used in varied ways. Due to the reduced g-forces, such systems can achieve significantly shorter revolution times (thus shorter scan periods) that are particularly advantageous in cardio examinations.

Furthermore, it is advantageous that the inventive system design allows the opening in the gantry housing (through which the patient must be moved for scanning) can be made significantly larger, such that there is a reduced feeling of claustrophobia in patients.

A significantly better heat distribution is additionally achieved due to the design of the anode ring 6, wherein the cooling system is now housed in a stationary region, and an optimal cooling of the anode surfaces is possible due to the manner of mounting the cooling channels.

The inventive design of a CT system also allows the slip ring, that conventionally had to carry and withstand the high voltage supply of the x-ray tube, can be designed significantly more cost-effectively.

Although modifications and changes may be suggested by those skilled in the art, it is the intention of the inventors to embody within the patent warranted hereon all changes and modifications as reasonably and properly come within the scope of their contribution to the art.

We claim as our invention:

1. A computed tomography system comprising:
a rotatably mounted support frame that is rotatable around a system axis;
a stationary x-ray tube, comprising an anode ring and at least one cathode ring, extending through 360° in a system plane that is perpendicular to the system axis, and an evacuated volume between the anode ring and the at least one cathode ring, said evacuated volume being at least partially delimited by a window;
a unitary system mounted on said support frame for co-rotation therewith, said unitary system comprising a laser that emits a laser beam that proceeds through said window to locally activate electron emission at successive locations along said at least one cathode ring as said support frame rotates, said electron emission proceeding through said window and causing x-ray emission from said anode ring at corresponding successive locations along said anode ring, and at least one x-ray emission-influencing component that interacts with and modifies said x-ray emission selected from the group consisting of an x-ray filter and a beam collimator; and
a radiation detector mounted on said support frame for co-rotation therewith opposite said unitary system, that detects said x-ray emission after interacting with said at lest one x-ray emission-influencing component.

2. A computed tomography system as claimed in claim 1 wherein said window is a quartz window.

3. A computed tomography system as claimed in claim 1 wherein said at least one cathode ring is mounted on an inside of said window in an interior of said x-ray tube, and wherein said laser beam emitted by said laser strikes said at least one cathode ring on a side thereof facing said window, and wherein said at least one cathode ring emits said electron emission, in response to activation by said laser beam, from an opposite side of said at least one cathode ring facing said anode ring.

4. A computed tomography system as claimed in claim 1 wherein said at least one cathode ring is disposed within said x-ray tube spaced from and opposite said window, and wherein said laser is mounted in said unitary system to cause said laser beam to strike a surface of said at least one cathode ring that faces said anode ring to produce said electron emission at said surface.

5. A computed tomography system as claimed in claim 4 comprising at least one mirrored surface located between said laser and said at least one cathode ring at a location that deflects said laser beam onto said surface of said at least one cathode ring.

6. A computed tomography system as claimed in claim 5 wherein said mirrored surface is located within said evacuated volume region of said x-ray tube.

7. A computed tomography system as claimed in claim 6 wherein said mirrored surface forms a ring.

8. A computed tomography system as claimed in claim 6 wherein said mirrored surface is connected to a negative potential.

9. A computed tomography system as claimed in claim 5 wherein said mirrored surface is located outside of said evacuated volume of said x-ray tube.

10. A computed tomography system as claimed in claim 1 wherein said, unitary system is a first unitary system and is located at a first angle position on said support frame, and wherein said computed tomography system comprises a second unitary system mounted at a second angle position on said support frame, offset from said first angle position, said second unitary system comprising a second laser that emits a second laser beam that proceeds through said window and causes electron emission from successive locations along said at least one cathode ring as said support frame rotates, said electron emission caused by said second laser beam also causing x-ray emission from said anode ring at successive locations along said anode ring, and said second unitary system comprising at least one second x-ray emission-influencing component, selected from the group consisting of an x-ray filter and a beam collimator, that interacts with and influences the x-ray radiation emitted from said anode ring caused by said electron emission caused by said second laser beam, and wherein said radiation detector is a first detector and wherein said computed tomography system comprises a second detector mounted on said support frame for co-rotation therewith, said second detector being offset from said first detector by an offset equal to the offset between said first and second unitary systems.

11. A computed tomography system as claimed in claim 10 wherein said first and second unitary systems are identical.

12. A computed tomography system as claimed in claim 10 wherein each of said first and second x-ray emission-influencing components produces a fan beam from the x-ray radiation interacting therewith, with the respective fan beams having identical angular magnitudes.

13. A computed tomography system as claimed in claim 1 wherein said x-ray tube comprises a first cathode ring and a second cathode ring operating respectively at different voltages, and wherein said unitary system is a first unitary system and is located at a first angle position on said support frame with said laser beam activating said electron emission from said first cathode ring, and wherein said computed tomography system comprises a second unitary system mounted at a second angle position on said support frame, offset from said first angle position, said second, unitary system comprising a second laser that emits a second laser beam that proceeds through said window and causes electron emission from successive locations along said second cathode ring as said support frame rotates, said electron emission caused by said second laser beam also causing x-ray emission from said anode ring at successive locations along said anode ring, and said second unitary system comprising at least one second x-ray emission-influencing component, selected from the group consisting of an x-ray filter and a beam collimator, that interacts with and influences the x-ray radiation emitted from said anode ring caused by said electron emission caused by said second laser beam, and wherein said radiation detector is a first detector and wherein said computed tomography system comprises a second detector mounted on said support frame for co-rotation therewith, said second detector being offset from said first detector by an offset equal to the offset between said first and second combined, unitary systems.

14. A computed tomography system as claimed in claim 13 wherein said first and second combined, unitary systems are identical.

15. A computed tomography system as claimed in claim 13 wherein each of said first and second x-ray emission-influencing components produces a fan beam from the x-ray radiation interacting therewith, with the respective fan beams having identical angular magnitudes.

16. A computed tomography system as claimed in claim 1 wherein said x-ray radiation-influencing component is a collimator, and wherein said collimator is a φ-collimator.

17. A computed tomography system as claimed in claim 1 wherein said x-ray radiation-influencing component is a collimator, and wherein said collimator is a z-collimator.

18. A computed tomography system as claimed in claim 1 wherein said detector is a multi-line detector.

19. A computed tomography system as claimed in claim 1 wherein said x-ray tube comprises at least one cooling channel proceeding through said anode ring in said system plane.

20. A computed tomography system as claimed in claim 1 wherein said at least one cathode ring is comprised of at least two segments, said at least two segments being respectively charged with different voltages.

21. A computed tomography system comprising:
a rotatably mounted support frame that is rotatable around a system axis;
a stationary x-ray tube, comprising an anode ring and at least one multi-emitter cathode ring, extending through 360° in a system plane that is perpendicular to the system axis, and an evacuated volume between the anode ring and the at least one multi-emitter cathode ring, said evacuated volume region being at least partially delimited by a window;
a unitary system mounted on said support frame for co-rotation therewith, said unitary system comprising a position transmitter that interacts with said multi-emitter cathode ring through said window to locally activate electron emission at successive locations along said at least one multi-emitter cathode ring as said support frame rotates, said electron emission proceeding through said evacuated volume and causing x-ray emission at corresponding successive locations along said anode ring, and at least one x-ray emission-influencing component that interacts with and modifies said x-ray emission, selected from the group consisting of an x-ray filter and a beam collimator; and
a radiation detector mounted on said support frame for co-rotation therewith opposite said combined unitary system that detects said x-ray emission after interacting with said x-ray emission-influencing component.

22. A computed tomography system as claimed in claim 21 wherein said position transmitter comprises a laser that emits a laser beam through said window and a plurality of photo-switches that cause said laser beam to activate said electron emission at said locations successively along said at least one cathode ring.

23. A computed tomography system as claimed in claim 21 wherein said position transmitter comprises a laser that emits a laser beam through said window and a plurality of Hall sensors that cause said laser beam to activate said electron emission at said locations successively along said at least one cathode ring.

* * * * *